United States Patent
Szabados

(10) Patent No.: US 11,099,109 B2
(45) Date of Patent: Aug. 24, 2021

(54) FIXATIVE

(71) Applicant: Andreas Szabados, Grünwald (DE)

(72) Inventor: Andreas Szabados, Grünwald (DE)

(73) Assignee: Biosepar Gesellschaft Fur Medizin—UND Labortechnik MBH, Muhldorf am Inn (DE)

( * ) Notice: Subject to any disclaimer, the term of this patent is extended or adjusted under 35 U.S.C. 154(b) by 190 days.

(21) Appl. No.: 16/077,269

(22) PCT Filed: Feb. 10, 2017

(86) PCT No.: PCT/EP2017/053089
§ 371 (c)(1),
(2) Date: Aug. 10, 2018

(87) PCT Pub. No.: WO2017/137616
PCT Pub. Date: Aug. 17, 2017

(65) Prior Publication Data
US 2019/0033180 A1    Jan. 31, 2019

(30) Foreign Application Priority Data
Feb. 10, 2016  (DE) .................. 10 2016 102 346.9

(51) Int. Cl.
| | | |
|---|---|---|
| *G01N 1/30* | (2006.01) | |
| *A61K 45/06* | (2006.01) | |
| *A61K 31/496* | (2006.01) | |
| *G01N 1/36* | (2006.01) | |

(52) U.S. Cl.
CPC .............. *G01N 1/30* (2013.01); *A61K 31/496* (2013.01); *A61K 45/06* (2013.01); *G01N 1/36* (2013.01)

(58) Field of Classification Search
CPC combination set(s) only.
See application file for complete search history.

(56) References Cited

U.S. PATENT DOCUMENTS

| | | | |
|---|---|---|---|
| 10,345,202 B2* | 7/2019 | Ulbrich | .................... G01N 1/31 |
| 2008/0057536 A1 | 3/2008 | Szabados et al. | |
| 2010/0209930 A1 | 8/2010 | Fernando | |
| 2015/0050689 A1 | 2/2015 | Gerigk et al. | |
| 2015/0140601 A1 | 5/2015 | Ulbrich et al. | |

FOREIGN PATENT DOCUMENTS

| | | |
|---|---|---|
| FR | 2684104 A1 | 5/1993 |
| WO | 2015171909 | 11/2015 |

OTHER PUBLICATIONS

International Search Report, PCT/EP2017/053089, dated May 22, 2017, 3 pages.
Written Opinion, PCT/EP2017/053089, dated May 22, 2017, 5 pages.

* cited by examiner

*Primary Examiner* — Heidi Reese
(74) *Attorney, Agent, or Firm* — Stinson LLP

(57) ABSTRACT

A fixative for the preservation of organic tissue and cell aggregates, comprising a hydrophilic denaturant for structural change of the molecules of the organic tissue, a lipophobic solvent, in which said denaturant is dissolved, and an amphiphilic infiltration agent which is dissolved in the solvent for dissolving fats on the surface of the biological tissue in order to accelerate a penetration of the denaturant into the biological tissue.

18 Claims, 1 Drawing Sheet

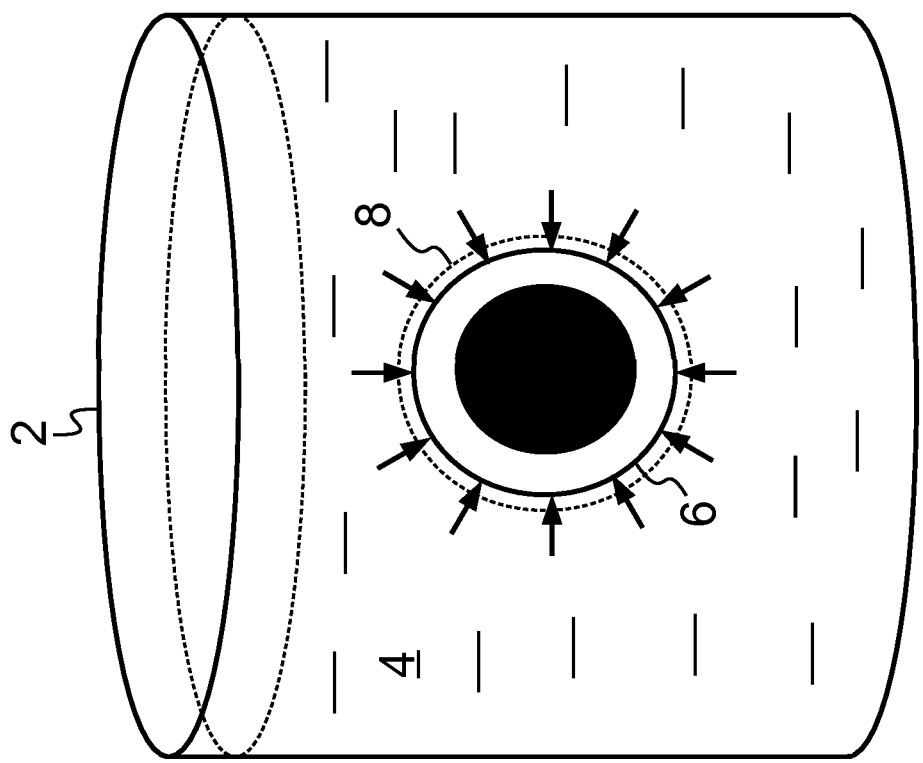

FIXATIVE

REFERENCE TO RELATED CASES

This application is a US national stage application based on PCT/EP2017/053089 filed Feb. 10, 2017, and claims priority to DE 10 2016 102 346.9 filed Feb. 10, 2016, the entire disclosures of which are expressly incorporated herein by reference.

FIELD OF INVENTION

The present invention relates to a fixative.

BACKGROUND

Various fixatives are, for example, known from DE 10 2012 101 896 A1. One of the disclosed fixatives comprises alcohol as a solvent, in which a polyamine is dissolved as denaturant. However, DE 10 2012 101 896 A1 also discloses that specific alcohols, such as ethanol, are disadvantageous as a solvent because they dehydrate the tissue to be preserved. A different disclosed fixative comprises water as the solvent, in which polyamine is dissolved as denaturant. However, particularly for the fixation of tissue with polyamines as denaturant dissolved in water, it is disadvantageous that the structural change of the organic tissue to be preserved, which is required for the preservation, takes place too slowly and as a result, for example, unwanted artifacts form, or the fixation process does not fully capture all the structures of the cells and the tissue.

SUMMARY OF THE INVENTION

The invention therefore addresses the problem of accelerating the effect of the denaturant without destroying the tissue to be preserved, thus improving the fixation.

According to one aspect of the invention, a fixative for preserving organic tissue and cell aggregates comprises a hydrophilic denaturant for structural change of the molecules of the organic tissue, a lipophobic solvent, in which said denaturant is dissolved, and an amphiphilic infiltration agent which is dissolved in the solvent for dissolving fats on the surface of the biological tissue in order to accelerate a penetration of the denaturant into the biological tissue.

BRIEF DESCRIPTION OF THE DRAWINGS

FIG. 1 shows a schematic depiction of a tissue body to be preserved in a fixative.

DETAILED DESCRIPTION OF PREFERRED EMBODIMENTS

The fixative according to the invention is based on the deliberation that a denaturant for use in a solvent is used in a dissolved state and acts hydrophilically. The denaturant must be able to dissolve in the solvent; the solvent can thus not be selected randomly. The solvent is not supposed to change the organic tissue to be preserved and should thus be selected to be lipophobic. On the other hand, fat decelerates the effect of the denaturant on the cell walls of the organic tissue to be preserved, increasing the probability of osmotic damage on the organic tissue to be preserved which in turn leads to the artifacts to be prevented (examples: Hemolytic effect, structural, biochemical, and morphological destruction of erythrocytes and other cells, cell structures, for example, also of protozoa, deterioration of the immunological properties).

For a quick penetration of the denaturant into the organic tissue to be preserved, it would thus be desirable if the fat on the cell walls were to be dissolved very quickly. With the fixative according to the invention, it is therefore proposed to additionally dissolve in the solvent an amphiphilic, i.e. a simultaneously lipophilic and hydrophilic, infiltration agent which can be dissolved in the solvent due to its hydrophilicity, and which dissolves the fat on the cell walls of the biological tissue to be preserved. The penetration of the denaturant into the biological tissue to be preserved is thus accelerated and the effect of the fixative improved, in order to capture all inter- and extracellular areas or components of the tissue to be preserved.

With the fixative according to the invention, satisfactory preservation results can be achieved even with polyamine, particularly also with urotropin, as a denaturant.

Preferably, water should be used as solvent because it does not affect the tissue to be preserved and is very inexpensive.

The amphiphilic infiltration agent should preferably have hygroscopic properties. As a result, the infiltration agent itself acts in a fixating manner and supports the actual denaturant in its preservation process without unfavorable denaturizing and hygroscopic properties to become manifest.

The amphiphilic infiltration agent can contain at least one short-chain alkanol with a maximum of ten carbon units. Short-chain alcohols have both polar OH groups and non-polar CH groups and thus act amphiphilically. The short-chain alkanol can be selected from methanol, ethanol, isopropanol, glycerin, and butanol.

The fixative according to the invention can contain 80 to 99.8% w/w of the solvent, 0.1 to 10% w/w of the denaturant, and 0.1 to 10% w/w of the infiltration agent. With these mixing ratios, an active infiltration is achieved by dissolving lipophilic membrane structures of the tissue. Due to the use of amphiphilic ethanol as a solvent, only a passive functional support is achieved with the initially mentioned fixative, which does not work or only partially works for many tissue types.

The infiltration agent can contain 0.1 to 10% w/w methanol and/or 0.1 to 10% w/w ethanol and/or 0.1 to 10% w/w isopropanol and/or 0.1 to 10% w/w glycerin and/or 0.1 to 10% w/w butanol. In particular, the fixative can contain three or four of the aforementioned alcohols and thus be a ternary or quaternary mixture.

The denaturant can contain a polyamine, particularly urotropin (also called hexamethylenetetramine or methenamine).

The fixative can further comprise an acidifier which is designed to release protons that react with the denaturant and thus form an aldehyde which in turn accelerates the preservation of the biological tissue. With the acidifier, it is possible to adjust the pH value of the fixative. For example, if only urotropin is used as a solvent in water, the pH value of this water solution is alkaline and unstable. For an effective fixative, the pH value should be adjusted to a stable value between 2.5 and 10, preferably below 8.

The acidifier for adjusting the pH value can be an organic acid, an inorganic acid, an acidically reacting salt, or a mixture thereof.

The organic acid can be selected from aliphatically saturated and unsaturated monocarboxylic acids, di- and tricarboxylic acids, aromatic carboxylic acids, for example, salicylic acids, benzoic acids, heterocyclic carboxylic acids, or mixtures thereof. Examples for possible organic acids are formic acid, acetic acid, propionic acid, lactic acid, oxalic acid, succinic acid, malonic acid, glutaric acid, tartaric acid, malic acid, citric acid, sorbic acid, ascorbic acid, and their mixtures.

The inorganic acid can be selected from hydrochloric acid, sulfuric acid, sulfurous acid, phosphoric acid, nitric acid, nitrous acid, and polythionic acids and their salts, as well as their mixtures.

The acidically reacting salt can be selected from quaternary ammonium compounds, ammonium chloride, and their mixtures.

In addition, bactericidally acting substances (such as sodium azide and quaternary ammonium compounds) can be added to the fixative. The addition of surfactants (anionic and cationic, nonionic and amphoteric surfactants—here also quaternary ammonium compounds with a surfactant effect) improves the ability of infiltration and penetration of the fixative according to the invention in the physiological and non-physiological milieu. 0.001-10.0% can be selected as concentration.

The solutions with the aforementioned contents can further be provided with fragrances and dye.

When compared to the conventional tissue and cell staining with formalin and other, previously used, conventional fixatives with many disadvantages, few or no artifacts are recorded with the fixative according to the invention. Many structures in the tissue, in the cells, and in the subcellular area are better stained with the following different staining techniques. Due to the use of the newly developed fixation concept, the serological-immunological and molecular biological examinations are also facilitated for the purpose of the improved possibility of the technical and diagnostic evaluation and further processing.

With the staining of the fixative, an optical differentiation with regard to other aqueous diagnostic agents and chemical solutions is achieved. As a result, the safety in the laboratory can be increased. The characteristic staining which is also supposed to be protected: Pink dye. The fragrances also serve the safety in the laboratory.

Due to the fixative according to the invention, there is no appreciable cross-linking of DNA and RNA and the proteins as is the case with most of the known fixatives according to the current prior art. This has enormous advantages for the DNA/RNA examinations, the molecular biological gene technology, but also for all other biotechnological works and examinations that have to do with protein structures. Fixatives that change primary, secondary, tertiary, or quaternary protein structures and frequently accomplish said change even irreversibly, do not meet the modern analytical and preparative work requirements and their quality management. Due to the strong, sometimes irreversible protein denaturation, not only an artificial barrier, hindrance, and a delay of the fixation process is achieved, but also artifacts are produced which, for example, during diagnosis, facilitate incorrectly positive or also incorrectly negative results. Formalin-containing and related fixatives are a good example for these disadvantages. At this point, reference should also be made to the pure alcohol-containing fixatives. The fixative according to the invention combines the advantages of all previous fixatives according to the prior art without exhibiting their disadvantages.

The above described properties, features, and advantages of this invention and the manner in which they are achieved shall become clearer and more obvious in connection with the following description of the embodiments which shall be explained in more detail using the drawing.

In the drawings, the same technical elements are denoted with the same reference signs and shall be described only once. The drawings are purely schematic and do particularly not represent the actual geometric relationships.

Reference is made to FIG. 1. It shows schematically a beaker 2, which accommodates a fixative 4 and a tissue 6 to be fixated with the fixative 4. The tissue 6 to be fixated can be a very fat-rich organ of a human, such as the central nervous system, the liver, the muscular system, the heart or the blood vessels. The rich fat content of the tissue 6 to be fixated is indicated in FIG. 1 by a dotted line 8 around the tissue 6 to be fixated.

In the present embodiment, the fixative 4 contains 98% of a solvent in the form of water, 1% of a denaturant in the form of urotropin, and 1% of an infiltration agent yet to be described.

For example, from DE 10 2012 101 896 A1, the preserving effect of urotropin is known. However, the preservation process is very slow, and particularly a high fat content 8 in the tissue 6 to be preserved significantly prolongs the preservation process.

For that reason, the infiltration agent is additionally dissolved in the solvent of the fixative 4. Its purpose is that of dissolving the fat content 8 of the tissue to be fixated, thus accelerating the infiltration of the denaturant. In order to make it possible for the infiltration agent to be dissolved in the fixative 4, it must additionally be selected to be hydrophilic; therefore, only amphiphilic substances qualify as infiltration agent.

In the present embodiment, a quaternary mixture of methanol, ethanol, isopropanol, and glycerin each in equal shares was selected for the infiltration agent. By adding this infiltration agent to the fixative 4, it was possible to significantly reduce the duration of the entire fixation and preservation process.

The use of an amphiphilic agent in the form of alcohol in the fixative is already known from DE 10 2012 101 896 A1, but the alcohol was used as the solvent itself. The alcohol indicated in said document, mixed with urotropin as an agent with a strongly polar and hydrophilic property, facilitates the passive penetration into the biological tissue.

The property of the alcohols, previously indicated as infiltration agent, dissolved in water expands the penetration of the fixation solution urotropin in a significantly improved manner, namely by softening/dissolving—and opening—the lipophilic membrane structure, and these alcohols themselves in the proposed concentration and mixtures also act as ideal fixatives—without having the unfavorable denaturizing and hygroscopic properties of the pure alcohol fixations, when the alcohol is used as the solvent itself.

In addition, the fixation properties of the alcohols dissolved in water together with urotropin in the indicated concentrations are present not only individually but also jointly cumulatively, resulting in a significant increase of the fixative quality and potency for all tissue types, regardless of the fat content.

In summary, the fixative according to the invention can be evaluated as follows:

Amphiphilic substances, such as the alcohols named as an example, are not used as the solvent containing the denaturant but as an auxiliary agent. The groups of substances indicated for the fixative according to the invention act in the indicated concentrations and the proposed mixing ratio fixatingly in an ideal manner in the physiological milieu as well as with adipose or fat-rich tissue.

The fixative according to the invention eliminates the previous disadvantages of the individual, fixatively acting amphiphilic substances because these disadvantages no longer come into effect due to the dissolving in a hydrophobic solvent.

The infiltration of the denaturant is actively achieved by dissolving lipophilic membrane structures of the tissue cells. With the use of amphiphilic substances as a solvent, only a passive functional support was achieved which does not work or only partially works for many tissue types.

The invention claimed is:

1. Fixative for the preservation of organic tissue and cell aggregates, comprising:
    a hydrophilic denaturant for structural change of the molecules of the organic tissue, wherein the denaturant is urotropin in a concentration of 0.1 to 10% w/w,
    a lipophobic solvent, in which said denaturant is dissolved, wherein the solvent is in a concentration of 80 to 99.8 w/w %,
    an amphiphilic infiltration agent which is dissolved in the solvent for dissolving fats on the surface of the biological tissue in order to accelerate a penetration of the denaturant into the biological tissue, wherein the infiltration agent is present in a concentration of 0.1 to 10 w/w %,
    an acidifier selected from the group consisting of an organic acid, an inorganic acid, an acidically reacting salt, or a mixture thereof, and
    a bactericidally acting substance,
    wherein the infiltration agent comprises at least three alcohols selected from the group consisting of methanol, ethanol, isopropanol, glycerin, and butanol.

2. Fixative according to claim 1, wherein the solvent contains water.

3. Fixative according to claim 1, wherein the amphiphilic infiltration agent has hygroscopic properties.

4. Fixative according to claim 1, wherein the amphiphilic infiltration agent contains at least one short-chain alkanol with a maximum of ten carbon units.

5. Fixative according to claim 4, wherein the short-chain alkanol is selected from methanol, ethanol, isopropanol, glycerin, and butanol.

6. Fixative according to claim 1, wherein the infiltration agent comprises:
    0.1 to 10% w/w methanol, and/or
    0.1 to 10% w/w ethanol, and/or
    0.1 to 10% w/w isopropanol, and/or
    0.1 to 10% w/w glycerin, and/or
    0.1 to 10% w/w butanol.

7. Fixative according to claim 1, wherein the solvent is water and the infiltration agent is a mixture of methanol, ethanol, isopropanol, and glycerin.

8. Fixative for the preservation of organic tissue and cell aggregates, comprising:
    a hydrophilic denaturant for structural change of the molecules of the organic tissue, wherein the denaturant is in a concentration of 0.1 to 10% w/w,
    a lipophobic solvent, in which said denaturant is dissolved, wherein the solvent is in a concentration of 80 to 99.8 w/w %, and
    an amphiphilic infiltration agent which is dissolved in the solvent for dissolving fats on the surface of the biological tissue in order to accelerate a penetration of the denaturant into the biological tissue, wherein the infiltration agent is present in a concentration of 0.1 to 10 w/w %.

9. Fixative according to claim 8, wherein the solvent contains water.

10. Fixative according to claim 8, wherein the amphiphilic infiltration agent has hygroscopic properties.

11. Fixative according to claim 8, wherein the amphiphilic infiltration agent contains at least one short-chain alkanol with a maximum of ten carbon units.

12. Fixative according to claim 11, wherein the short-chain alkanol is selected from methanol, ethanol, isopropanol, glycerin, and butanol.

13. Fixative according to claim 8, wherein the infiltration agent comprises:
    0.1 to 10% w/w methanol, and/or
    0.1 to 10% w/w ethanol, and/or
    0.1 to 10% w/w isopropanol, and/or
    0.1 to 10% w/w glycerin, and/or
    0.1 to 10% w/w butanol.

14. Fixative according to claim 13, wherein the infiltration agent comprises at least three alcohols selected from the group of said methanol, ethanol, isopropanol, glycerin, and butanol.

15. Fixative according to claim 8, wherein the denaturant contains a polyamine.

16. Fixative according to claim 15, wherein the polyamine comprises urotropin.

17. Fixative according to claim 8, further comprising an acidifier.

18. Fixative according to claim 8, wherein the denaturant is urotropin, the solvent is water, and the infiltration agent is a mixture of methanol, ethanol, isopropanol, and glycerin.

* * * * *